DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED OCTOBER 3, 1972

903 O.G. 5

T903,007
PREPARATION OF SUBSTITUTED CYCLOHEXADIENONES

Hans K. Dietl and Howard S. Young, both of P.O. Box 511, Kingsport, Tenn. 37901

Filed July 9, 1971, Ser. No. 161,355
**Int. Cl. C07c *49/64***
U.S. Cl. 260—396 N
No Drawing. 9 Pages Specification

Substituted cyclohexadienones having the structural formula

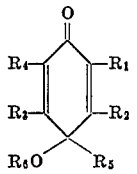

wherein $R_1$, $R_2$, $R_3$ and $R_4$ are the same or different and each of $R_1$, $R_2$, $R_3$ and $R_4$ may be hydrogen, alkyl, aryl, halogen, or alkoxy; $R_5$ is alkyl, aryl, or halogen, and $R_6$ is alkyl, are prepared by reacting a para-substituted phenol having at least one substitution in the ortho position, with manganese dioxide in an aqueous sulfuric acid-straight or branched chain alcohol solution or reaction medium. The substituent occupying the para-position on the para-substituted phenol starting material must not be hydrogen. Among typical suitable, readily available and relatively inexpensive alcohols which may be employed as the alcohol component of the acid-alcohol reaction medium may be mentioned straight or branched chain alcohols such as methanol, ethanol, n-propanol, isopropanol, n-butanol, tertiary-butanol, pentanols, and the like. The cyclohexadienones prepared in accordance with the invention may be readily converted by known reactions into a number of valuable food antioxidants and related products.